United States Patent
Secovich et al.

(10) Patent No.: US 8,512,274 B2
(45) Date of Patent: Aug. 20, 2013

(54) DEVICE FOR COOLING CUTANEOUS AND SUB-CUTANEOUS TISSUES AND METHOD OF MANUFACTURE THEREOF

(75) Inventors: Matthew Secovich, Southwick, MA (US); StJohn D McGrath, Southwick, MA (US)

(73) Assignees: Matt Secovich, Southwick, MA (US); Donald McGrath, Southwick, MA (US)

( * ) Notice: Subject to any disclaimer, the term of this patent is extended or adjusted under 35 U.S.C. 154(b) by 0 days.

(21) Appl. No.: 13/102,736

(22) Filed: May 6, 2011

(65) Prior Publication Data
US 2011/0275993 A1    Nov. 10, 2011

Related U.S. Application Data

(60) Provisional application No. 61/333,078, filed on May 10, 2010.

(51) Int. Cl.
*A61M 37/00* (2006.01)

(52) U.S. Cl.
USPC .................. 604/23; 604/24; 604/113; 601/46; 607/104

(58) Field of Classification Search
USPC .................. 604/113, 23–26; 601/46, 15–16; 607/104, 96, 107
See application file for complete search history.

(56) References Cited

U.S. PATENT DOCUMENTS
7,438,745 B2 * 10/2008 Deane et al. ...................... 95/96

FOREIGN PATENT DOCUMENTS
WO    WO0100367 A2      1/2001
WO    WO 0103637 A2 *   1/2001
WO    WO2004105674 A1   12/2004

* cited by examiner

*Primary Examiner* — Theodore Stigell
(74) *Attorney, Agent, or Firm* — Cantor Colburn LLP (57) ABSTRACT

A device for cooling cutaneous and sub-cutaneous tissues includes an applicator. The applicator has a head and a handle. The head has ports that are operative to dispense a pressurized fluid. The device also has a pressurizing section where the pressurizing section comprises at least one pump. The pump delivers pressurized fluid at a pressure of less than or equal to about 2 bars to the applicator.

25 Claims, 6 Drawing Sheets

Section along AA'

Figure 6

DEVICE FOR COOLING CUTANEOUS AND SUB-CUTANEOUS TISSUES AND METHOD OF MANUFACTURE THEREOF

CROSS-REFERENCE TO RELATED APPLICATIONS

This application claims priority to U.S. Provisional Application No. 61/333,078 filed on May 10, 2010, the entire contents of which are hereby incorporated by reference.

BACKGROUND

This disclosure relates to a device that cools cutaneous and sub-cutaneous tissues. This disclosure also relates to a method of manufacturing the device.

Increased cooling in cutaneous and sub-cutaneous tissues can lead to improved blood flow to the cutaneous tissues and sub-cutaneous tissues is useful for maintaining a smooth appearance of the cutaneous tissues and sub-cutaneous tissues and for minimizing wrinkles. It is also useful for a quick recovery from damage to the cutaneous tissues and sub-cutaneous tissues caused by abrasions, cuts, injuries, and the like.

Direct cooling of the cutaneous tissues and sub-cutaneous tissues generally causes vasoconstriction, related to the extent and duration of cooling, that follows a deceivingly simple pattern of an immediate vasoconstriction followed by a slow further reduction in blood flow, disguising the multiplicity of mechanisms acting to bring it about. Although the cutaneous vasoconstriction accompanying local cooling is part of local control, intrinsic to the tissue, important contributions arise from sensory and autonomic nerves. Indeed, local cooling in the presence of blockade of either sensory nerves or sympathetic vasoconstrictor function reverses the vasoconstriction seen at the onset of local cooling to a transient vasodilation. The mechanism for this vasodilation is not known.

Because it is transient and dependent on the rate of cooling, a depletable substance rather than biophysical effects of the lower temperature is suggested. It can be provoked in neurally intact tissue with a sufficient rate and extent of cooling. This implies that sensory nerves, likely originating from cold receptors, inhibit an intrinsic vasodilator response to cooling. The vasodilation can lead to increased blood flow to the site of an injury when it is subjected to cooling.

Often commercially available devices that are used for cooling the cutaneous tissues and sub-cutaneous tissues operate at air pressures that are greater than 5 bars. Such air pressures can further damage the cutaneous tissues and sub-cutaneous tissues. In addition, such devices are heavier than ten pounds and are thus not portable. It is therefore desirable to have a device that can cool the cutaneous tissues and/or sub-cutaneous tissues while using a fluid pressure of less than 1 bar and that are light enough to be portable by the average human being.

SUMMARY

Disclosed herein is a device comprising an applicator; the applicator having a head and a handle; the head having ports that are operative to dispense a pressurized fluid; and a pressurizing section; the pressurizing section comprising at least one pump; wherein the pump delivers pressurized fluid at a pressure of less than or equal to about 2 bars to the applicator.

Disclosed herein too is a method comprising delivering to a patient a pressurized fluid at a pressure of less then or equal to about 2 bars; the pressurized fluid being generated by a device comprising an applicator; the applicator having a head and a handle; the head having ports that are operative to dispense a pressurized fluid; and a pressurizing section; the pressurizing section comprising at least one pump; wherein the pump delivers pressurized fluid at a pressure of less than or equal to about 2 bars to the applicator.

Disclosed herein too is a method comprising disposing an applicator and a pressurizing section to be in fluid communication with one another; where the applicator has a head and a handle; the head having ports that are operative to dispense a pressurized fluid; and wherein the pressurizing section comprises at least one pump; wherein the pump delivers pressurized fluid at a pressure of less than or equal to about 2 bars to the applicator.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Disclosed herein is a portable device that is capable of supplying pressurized air to the cutaneous tissues and sub-cutaneous tissues. The portable device generally delivers a fluid to the cutaneous tissues and sub-cutaneous tissues at a pressure of less than or equal to about 2 bars, specifically at a pressure of less than or equal to about 1 bar. Because of the light-weight of the device, it can easily be transported by the average person. It is particularly advantageous in that it can be placed next to the bed of an injured patient, who can then maneuver it for use when necessary. The device can be easily used and manipulated by a patient or an assistant (e.g., a nurse, a doctor, a medical orderly, and the like).

In an exemplary embodiment, the portable device and the applicator can be manipulated by the person using it (i.e., a patient). Its light weight and flexibility permit self treatment and self administration by the patient.

Figure 1:
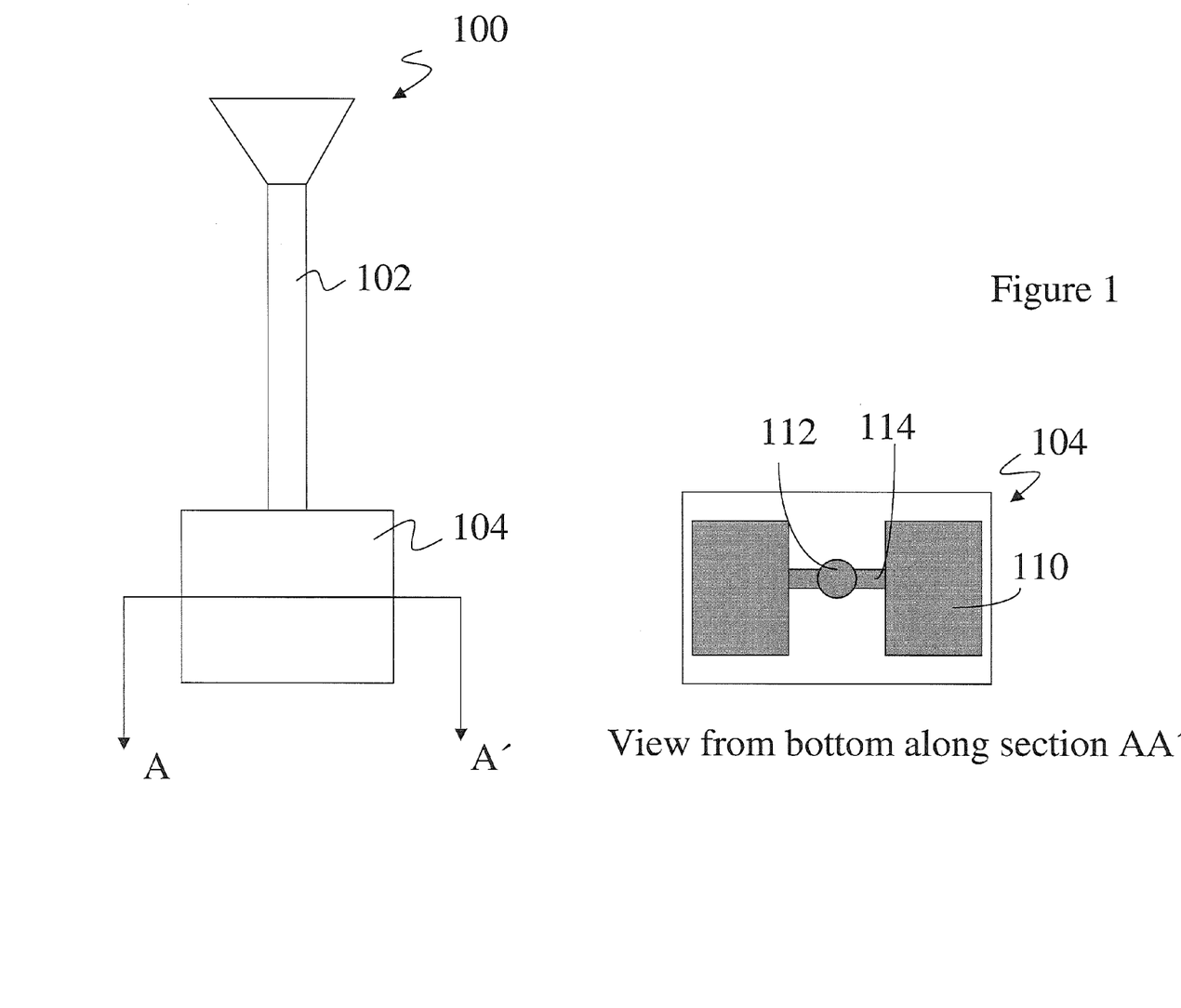
FIG. 1 is a schematic diagram depicting an exemplary device that comprises the applicator and the pressurizing section that are detachably attached to one another.
Figure 2:
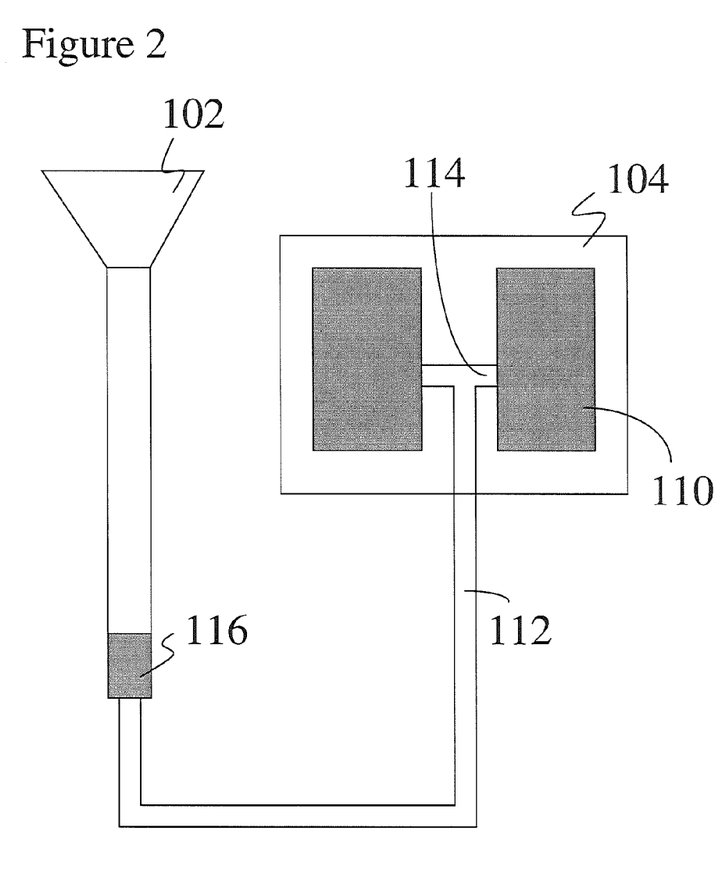
FIG. 2 is a schematic diagram depicting an exemplary device that comprises the applicator and the pressurizing section when they are connected to one another by a conduit.

With reference now to the FIGS. 1 and 2, the device 100 comprises an applicator 102 that is in fluid communication with a pressurizing section 104. In one embodiment, the applicator 102 and the pressurizing section 104 are in physical communication with each other in a single piece. The applicator 102 and the pressurizing section 104 are detachably attached and can be separated from one another when desired as shown in the FIG. 2. A flexible hose 112 contacts both the pressurizing section 104 and the applicator 102. The flexible hose 112 permits a pressurized fluid from the pressurizing section 104 to be delivered to the applicator 102. In one embodiment, the pressurized fluid is air. The flexible hose 112 can be folded into a casing (not shown) that houses the pressurizing section 104. The flexible hose 112 can be connected to the applicator 102 and the pressurizing section 104 using a quick connect coupling 116, thus allowing the flexible hose 112 to be quickly attached or detached from the applicator 102 and/or the pressurizing section 104.

The flexible hose 112 can be manufactured from an elastomer. Examples of suitable elastomers are polybutadiene, polyisoprene, nitrile rubbers, perfluoroethylene elastomers, polysiloxanes, polychloroprenes, or the like, or a combination comprising at least one of the foregoing elastomers. Exemplary elastomers for use in the hose are perfluoroethylene elastomers or polysiloxanes because of their ability to resist bioadhesion.

As noted above, the pressurized fluid is air. In one embodiment, the pressurized fluid can be an inert gas such as helium, argon, xenon, nitrogen, or the like. In another embodiment, which will be discussed later, the pressurized fluid can have entrained in it a biologically active agent.

Figure 3:
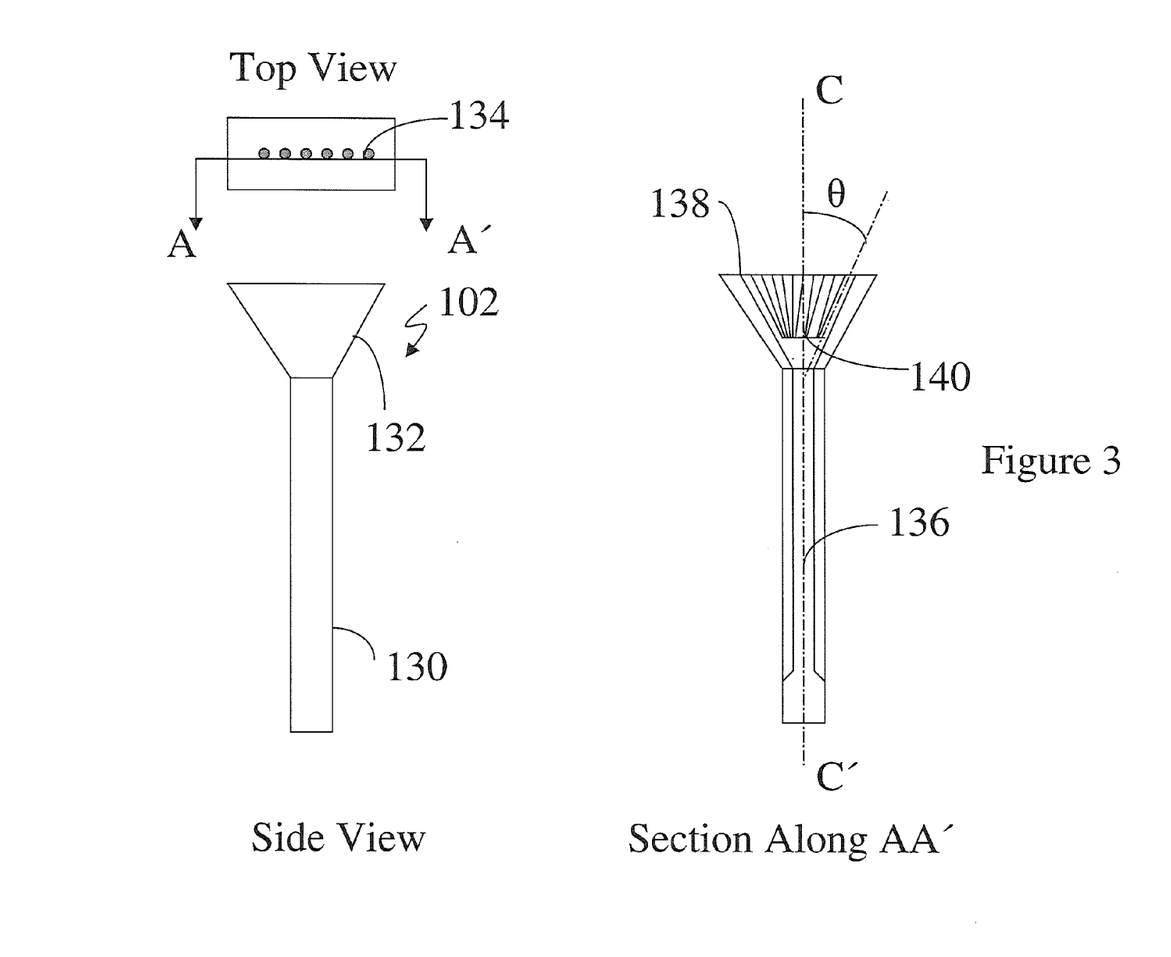
FIG. 3 is a schematic diagram of the applicator (shown in the top view and the side view) and a section along AA'.

The applicator 102 is shown in the FIG. 3. The FIG. 3 depicts a top view and a side view of the applicator 102. The FIG. 3 depicts a section of the applicator taken along AA' in the top view. The applicator 102 comprises a head 132 and a handle 130. The head can have a cross-sectional area that is about 2 to about 3 times the cross-sectional area of the handle. The handle 130 is a conduit 136 that is fixedly attached or detachably attached to the head 132. The head 132 has a number of ports 134 disposed in the surface. The ports 134 are in fluid communication with the pressurizing section 104 via the conduit in the handle 130 and the flexible hose 112. The ports are generally about 5 millimeters or less in diameter, specifically about 3 millimeters or less in diameter, more specifically about 1.5 millimeter of less in diameter, and more specifically up to about 100 micrometers of less in diameter. The head can have up to at least about 50 ports, specifically up to at least about 35 ports, more specifically up to at least about 20 ports, and more specifically up to at least about 5 ports.

As seen in the FIG. 3, the ports in the head 132 can be inclined at an angle θ to the axis CC' of the conduit 136. In another embodiment, the ports in the head 132 are parallel to the axis CC' of the conduit 136. The ports can be fixed in shape or can have a variable shape. The ports can be nozzle-shaped with a diameter than is gradually reduced towards the outer surface 138 from the inner surface of the head 132. When the ports are nozzle-shaped such that the diameter is gradually reduced towards the outer surface 138 from the inner surface, the volume of pressurized fluid emanating from the ports is reduced. However, the velocity of the pressurized fluid and the amount of cooling provided by the pressurized fluid is increased.

Figure 4:
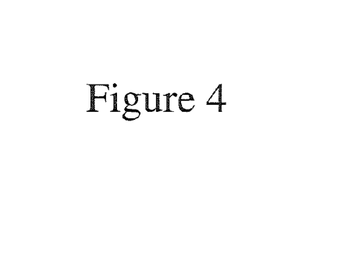
FIG. 4 is another schematic diagram of the applicator showing a section along AA' of the FIG. 3.
Figure 5:
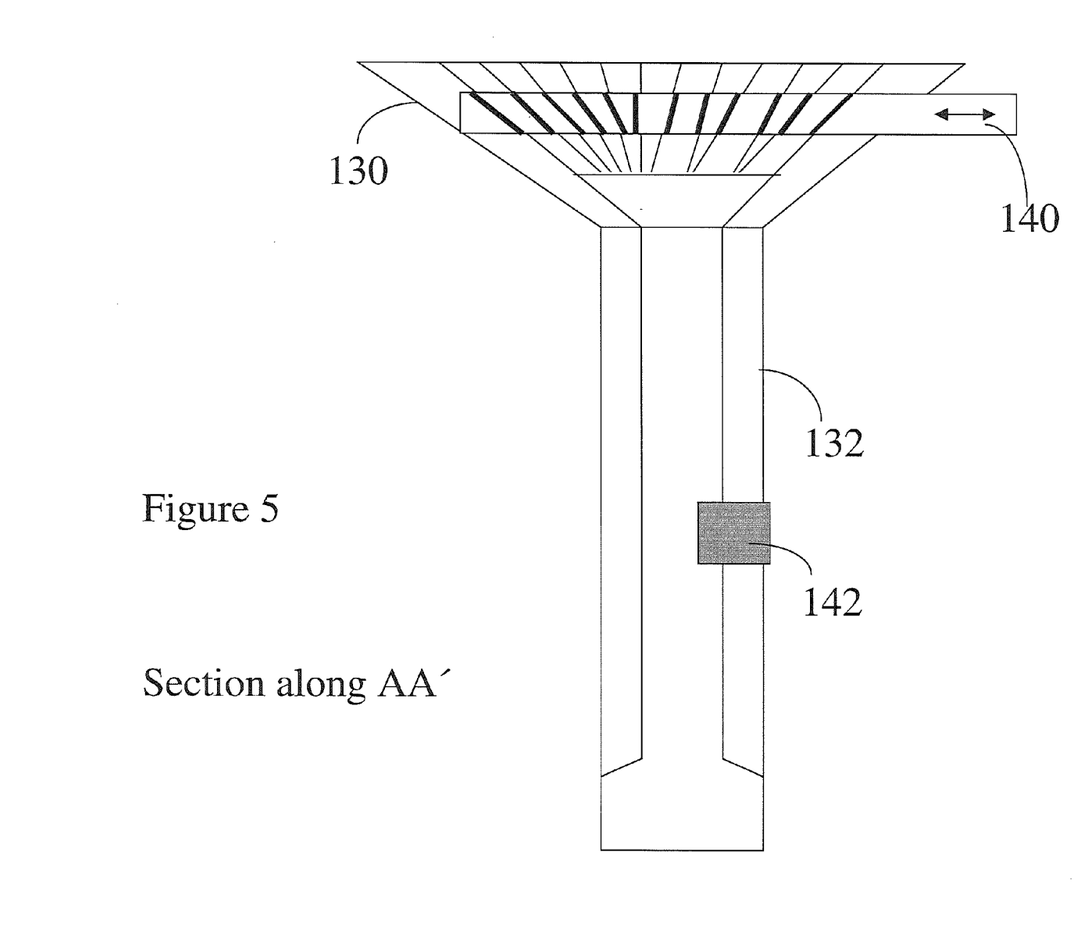
FIG. 5 is another schematic diagram of the applicator showing a section along AA' of the FIG. 3.

The ports can also be nozzle shaped with a diameter than is gradually reduced towards the inner surface from the outer surface of the head 132 as shown in the FIG. 5. The FIG. 5 depicts another exemplary cross-sectional view of the applicator from the section AA' in the FIG. 3. In one embodiment, the head 132 can have a diameter that is constant throughout the port as can be seen in the FIG. 4. The FIG. 4 depicts another exemplary cross-sectional view of the applicator from the section AA' in the FIG. 3. The ports direct pressurized fluid from pressurizing section 104 to the cutaneous tissues and sub-cutaneous tissues or to other parts of the body as desired.

In one embodiment, the diameter and the shape of the ports can be changed during the operation of the device 100. As shown in the FIG. 5, a slideable throttle 140 can be moved in and out of a slot in the applicator 102 to increase or decrease the flow of the pressurized fluid to the cutaneous tissues and sub-cutaneous tissues. The throttle 140 has ports similar to the size of the ports disposed in the head of the applicator. By moving the throttle such that its ports are concentrically aligned with the ports in the head, the volume of pressurized fluid can be maximized. On the other hand, by moving the throttle such that its ports are eccentrically aligned with the ports in the head, the flow of pressurized fluid can be reduced or minimized. The throttle can have screw threads on its outer surface and can be rotated to slide in or out of the slot in the applicator 102 thereby changing the size of the fluid channel in the port.

With reference to the FIG. 5, the applicator 102 can also have a port 142 on the side. The port 140 can be in fluid communication to a storage vessel that contains biologically active agents. One or more biologically active agents can be supplied to the cutaneous and sub-cutaneous tissues by the applicator 102 as a result of the venturi action brought about by the flow of the pressurized fluid in the conduit 136. The biologically active agent can be in the form of a fluid (e.g., a liquid, a gas, a suspension, a solution, a dispersion, droplets, a mist, an aerosol, and the like), a cream, a paste, a powder, or the like. In one embodiment, one or more biologically active agents can be drawn in to the conduit 136 by the venturi action along with one or more liquids and the mixture of the biologically active agents and the liquids can undergo mixing in the conduit 136 prior to being delivered to the cutaneous or sub-cutaneous tissue.

Examples of suitable biologically active agents are antiproliferative/antimitotic agents including natural products such as vinca alkaloids (e.g., vinblastine, vincristine, and vinorelbine), paclitaxel, epidipodophyllotoxins (e.g., etoposide, teniposide), antibiotics (e.g., dactinomycin, actinomycin D, daunorubicin, doxorubicin and idarubicin), anthracyclines, mitoxantrone, bleomycins, plicamycin, mithramycin and mitomycin, enzymes (L-asparaginase, which systemically metabolizes L-asparagine and deprives cells which do not have the capacity to synthesize their own asparagine), antiplatelet agents such as G(GP) IIb/IIIa inhibitors and vitronectin receptor antagonists, anti-proliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC), anti-proliferative/antimitotic antimetabolites such as folic acid analogs (e.g., methotrexate), pyrimidine analogs (e.g., fluorouracil, floxuridine, cytarabine), purine analogs and related inhibitors (e.g., mercaptopurine, thioguanine, pentostatin and 2-chloro deoxyadenosine {cladribine}), platinum coordination complexes (e.g., cisplatin, carboplatin), procarbazine, hydroxyurea, mitotane, aminoglutethimide, hormones (e.g., estrogen), anti-coagulants (e.g., heparin, synthetic heparin salts and other inhibitors of thrombin), fibrinolytic agents (e.g., tissue plasminogen activator, streptokinase and urokinase), aspirin, dipyridamole, ticlopidine, clopidogrel, abciximab, antimigratory, antisecretory (e.g., brevelpin), anti-inflammatory: such as adrenocortical steroids (e.g., cortisol, cortisone, fludrocortisone, prednisone, prednisolone, 6α-methylprednisolone, triamcinolone, betamethasone, and dexamethasone), non-steroidal agents (e.g., salicylic acid derivatives such as aspirin, para-aminophenol derivatives such as acetominophen, indole and indene acetic acids (e.g., indomethacin, sulindac, etodalac), heteroaryl acetic acids (e.g., tolmetin, diclofenac, ketorolac), arylpropionic acids (e.g., ibuprofen and derivatives), anthranilic acids (e.g., mefenamic acid, meclofenamic acid), enolic acids (e.g., piroxicam, tenoxicam, phenylbutazone, oxyphenthatrazone), nabumetone, gold compounds (e.g., auranofin, aurothioglucose, gold sodium thiomalate), immunosuppressives (e.g., cyclosporine, tacrolimus (FK-506), sirolimus (e.g., rapamycin, azathioprine, mycophenolate mofetil), angiogenic agents such as vascular endothelial growth factor (VEGF), fibroblast growth factor (FGF), angiotensin receptor blockers, nitric oxide donors, anti-sense oligionucleotides and combinations thereof, cell cycle inhibitors, mTOR inhibitors, and growth factor receptor signal transduction kinase inhibitors, retenoids, cyclin/CDK inhibitors, HMG co-enzyme reductase inhibitors (statins), and protease inhibitors.

As the pressurized fluid is transported through the conduit 136 some of the biologically active agent is drawn into the applicator as a result of the vacuum created in the port 140 by the Bernoulli effect (venturi action). The pressurized fluid entrained with the biologically active agent is then disposed on the cutaneous tissues and/or sub-cutaneous tissues of the patient to effect a cure.

In one embodiment, the applicator 102 can have a plurality of application points through which pressurized air can be applied to the body of a patient. The applicator 102 can also be provided with vibratory characteristics and can be used to provide heat to the point of contact on the skin. The applicator 102 may also be a smart applicator having a positioning system enclosed therein. The smart applicator can be used to provide relief at precise locations within the body of a living being. An example of smart applicator is one that contains communication equipment that permits the applicator to communicate with global positioning systems.

An example of such an applicator 102 may be seen in the FIG. 6. The FIG. 6 shows the applicator 102 having and handle 130 and legs 202 that are in communication with the handle. Each leg 202 is fitted with a head 132 through which pressurized air may be released. As seen in the FIG. 6, each head 132 has a port 134 through which pressurized air may contact the skin of a patient. The flexible hose 112 can contact the applicator 102 via a quick coupling 116 as detailed above with respect to FIGS. 1 and 2.

The applicator may be provided with a plurality legs 202. The applicator 102 can have 2, 3, 4, 6 or more legs, where each leg is fitted with a head 132 having ports 134 through which pressurized air is released. The head may also contain heaters (not shown) for heating the surface of the skin.

The applicator may have a motor (not shown) that can transmit vibrations to the body of the patient. The handle of the applicator may also house communications equipment that can communicate with global positioning systems to help improve location of tissues on the body so that the pressurized air and/or vibrations and/or heat can be accurately applied.

The applicator 102 can be manufactured from a wide variety of metals, ceramics, polymers or combinations thereof. It is generally desirable for the applicator 102 to have a smooth outer surface 138 so that it does not abrade any tissue as it is passed along the surface of the body. Examples of metals that can be used in the applicator are stainless steel, aluminum, copper, brass, or the like, nickel titanium shape memory alloys, or the like, or a combination comprising at least one of the foregoing metals. Examples of suitable ceramics are silica, quartz, alumina, titania, zirconia, or the like, or a combination comprising at least one of the foregoing ceramics. Examples of suitable polymers are polyolefins, polycarbonates, polymethylmethacrylates, polyacrylates, polyetherimides, polyetherketones, polyesters, polytetrafluoroethylenes, polysiloxanes, polyether ether ketones, or the like, or a combination comprising at least one of the foregoing polymers. An exemplary metal is aluminum. An exemplary polymer is polytetrafluoroethylene. In one embodiment, the exemplary metal is aluminum with a coating of polytetrafluoroethylene or polysiloxane. The polytetrafluoroethylene coating or polysiloxane coating is detachable from the metal head. It can be reattached to the head by thermoforming or by using an adhesive. Alternatively, the original coating can be removed and a new coating can be sprayed onto the head. Using a removable coating on the head allows for disinfection of the coating and the head to prevent the transfer of disease carrying bacteria or viruses from one patient to another.

Figure 6:
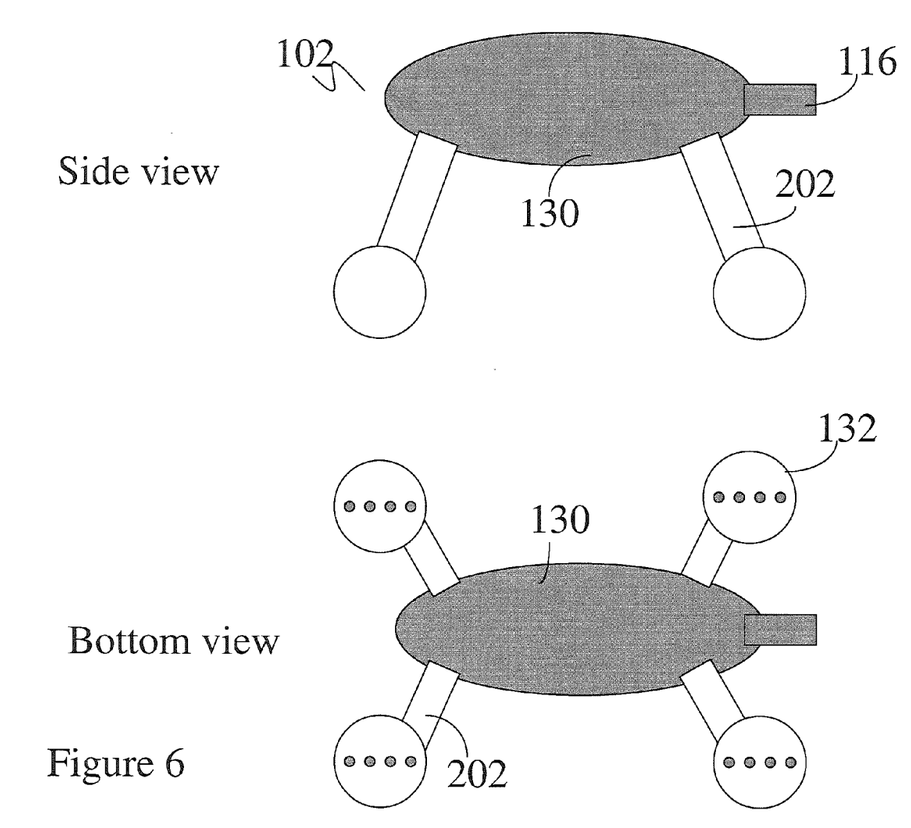
FIG. 6 is another schematic diagram of an applicator that has legs and a handle and is capable of intelligent positioning, vibration and applying heat to the skin of a patient.

In one embodiment, the legs 202 of the applicator shown in the FIG. 6 or the handle of the applicator shown in the FIG. 3 may be made of a flexible material such as an elastomer. The surface of the applicator may also be textured if desired to provide an ability to gently scratch the skin. Scratching can provide comfort against irritation that is generally encountered after irritation.

The pressurizing section 104 generally contains a pump 110 that can deliver pressurized fluid to the applicator at a pressure of up to about 2 pounds, specifically at a pressure of up to about 1 pound. In one embodiment, the pressurizing section 104 contains a plurality of pumps. The plurality of pumps can be operated simultaneously or sequentially. In an exemplary embodiment, the pressurizing section 104 contains at least two pumps.

The pressurized fluid output from both pumps is delivered to the conduit 136 of the applicator 104. By delivering the pressurized fluid at a pressure of less than or equal to about 1 pound, damage to tissue is avoided. The pressurizing section 104 and the applicator 102 may contain valves (not shown) to facilitate control of the pressurized fluid.

The pressurized fluid is delivered to the applicator at a substantially constant temperature over an extended period of time during the use of the device. By delivering the pressurized fluid at a constant temperature over an extended period of time, the patient receives a constant supply of a fluid that cools the cutaneous tissues and sub-cutaneous tissues and increases circulation. An extended period of time as defined herein refers to time periods of greater than or equal to about 30 minutes, specifically greater than or equal to about 60 minutes.

While the pressurized fluid is generally delivered to cutaneous tissues and/or subcutaneous tissues at a fairly constant temperature, the applicator may be used to deliver a cooled fluid or a heated fluid to a patient. This can be done when the therapeutic benefits of delivering a cooled fluid or a heated fluid to a patient exceed the benefits of delivering a fluid that is at an ambient temperature.

As noted above, the pressurizing section 104 is detachably attached to the applicator 102. In one embodiment, the pressurizing section 104 is not attached to the applicator and is in fluid communication with the applicator 102 via the hose 112. The pressurizing section 104 and the pumps contained therein are ventilated so as to avoid heating. The use of the pump 110 is advantageous in that the air supplied to the patient is at a constant temperature. The pumps do not heat up upon being operated significantly for extended periods of time (e.g., time periods exceeding 30 minutes to 2 hours). In one embodiment, the pressurizing section 104 is effectively ventilated to supply pressurized air for a period of over 30 minutes at a temperature that does not fluctuate by an amount of ±1° C. In another embodiment, the pressurizing section 104 is effectively ventilated to supply pressurized air for a period of over 60 minutes at a temperature that does not fluctuate by an amount of ±2° C.

The pumps are not subjected to special cooling (such as cooling fluids) and operate at a given temperature only as a result of passive cooling provided by ambient air.

The pump 110 or the plurality of pumps 110 are light enough to be portable. In one embodiment, the pumps 110 are less than or equal to about 10 pounds apiece, specifically less than or equal to about 5 pounds apiece, and more specifically less than or equal to about 2 pounds apiece, while delivering pressurized fluid at about 2 bars or less, specifically at about 1 bar or less at a constant temperature for a period of greater than or equal to about 30 minutes, specifically for a period of greater than or equal to about 60 minutes.

In one embodiment, the pump 110 is a fixed pressure pump with no pressure regulating abilities. In another embodiment, the output pressure of the pump 110 may be regulated. The use of a fixed pressure pump 110 has a number of advantages over other devices including compressors. The pump 110, when used in the pressurizing section 104 does not use a particulate filter or an oil filter. The pressurizing section 104 and the pump 110 does not store pressurized air as does a compressor. As a result, the pressurizing section 104 and the device 100 is very light and can be easily transported and manipulated. The pump generally has a weight less than or equal to about 15 pounds, specifically less than or equal to about 12 pounds and more specifically less than or equal to about 10 pounds.

The device 100 and the pressurizing section 104 are very silent and operate without any vibration. As a result, they can be used in a hospital room without disturbing neighboring patients. They can also be used indoors without disturbing the household. The pump 110 generally produces less than 50 dB of noise, specifically less than or equal to about 47 dB, specifically less than or equal to about 45 dB, and more specifically less than or equal to about 40 dB at a distance of 1 meter from the center of the pump. The pumps have minimal vibration. In one embodiment, the pump 110 and the pressurizing section 104 display a vibration of less than or equal to about 60 Hz, and specifically less than or equal to about 50 Hz. In short, the pressurized air is pulsed at a rate of frequency input that is less than or equal to about 60 Hz, and specifically less than or equal to about 50 Hz.

The pump 110 may be a diaphragm pump, a linear pump, a centrifugal pump, a piston driven pump, a rocking piston pump, or the like. An exemplary pump is a linear pump. A commercially available version of the pump is manufactured by GAST.

In one embodiment, the pressurizing section 104 can be a cabinet that houses the pumps. In another embodiment, the pressurizing section 104 can be a cabinet that comprises an electrical cabinet section and a pneumatic cabinet section (not shown) that are separated from each other. The electrical cabinet section contains electrical wires and other electrical accessories for the pumps. The pneumatic cabinet section contains the pumps and associated valves. This arrangement is advantageous in that any heat generated in the electrical cabinet section is kept away from the pumps contained in the pneumatic cabinet section. A grill type vent may be provided on both the electrical cabinet section and the pneumatic cabinet section to permit heat to escape.

The pressurizing section 104 generally comprises a boxed enclosure having a height or width of greater than or equal to about 20 inches, specifically greater than or equal to about 25 inches and more specifically greater than or equal to about 30 inches. If the height is greater than or equal to about 20 inches, then the width is less than or equal to 30 inches, specifically less than or equal to about 25 inches and more specifically less than or equal to about 20 inches.

The design shown in the FIGS. 1-5 is advantageous in that it is light-weight and capable of being transported by an average-sized human being. The device 100 can supply pressurized fluid containing an optional biologically active agent at a pressure of less than or equal to about 1 bar. The pressurized fluid can be supplied for an extended period of time exceeding 30 minutes without any substantial fluctuation in temperature. In one embodiment, the housing section 104 can be mounted on wheels to aid in the portability of the device 100.

In one embodiment, the device can be manufactured by connecting an applicator having a plurality of ports disposed thereon to a pressurizing section. The pressurizing section contains at least one pump that delivers pressurized fluid at a constant temperature at a pressure of less than or equal to about 2 bars, specifically less than or equal to about 1 bar. The pressurizing section and the applicator are in fluid communication via a flexible hose. The use of light weight pumps permits the device 100 to do away with filters, condensation units and the like, which are typically used in units or devices that employ air compressors. The pressurized air delivered to a patient from an applicator is clean without any entrained oils and fuels and is delivered at a substantially constant temperature and pressure.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A device comprising:

an applicator; the applicator having a head and a handle; the head having ports that are operative to dispense a pressurized fluid; and a pressurizing section; the pressurizing section comprising at least one pump; the at least one pump being devoid of a filter, wherein the pump delivers the pressurized fluid at a pressure of less than or equal to 2 bars to the applicator; where the pump has a weight of less than or equal to 10 pounds and produces less than 50 dB of noise when measured at a distance of 1 meter from a center of the pump.

2. The device of claim 1, wherein the head has 1 to 50 ports.

3. The device of claim 2, wherein the head has 2 to 10 ports.

4. The device of claim 1, where the device delivers pressurized fluid at a substantially constant temperature for a time period of greater than or equal to 30 minutes.

5. The device of claim 4, where the device delivers pressurized fluid at a substantially constant temperature for a time period of greater than or equal to 60 minutes.

6. The device of claim 1, wherein the pump delivers pressurized fluid at a pressure of less than or equal to 1 bar to the applicator.

7. The device of claim 1, wherein the pump is a linear pump.

8. The device of claim 1, wherein the pump is a diaphragm pump or a centrifugal pump.

9. The device of claim 1, wherein the pressurizing section comprises two or more pumps.

10. The device of claim 9, wherein the two or more pumps operate simultaneously.

11. The device of claim 1, wherein the handle comprises a port that is in fluid communication with a source of a biologically active agent.

12. The device of claim 1, wherein the device is capable of delivering a pressurized fluid entrained with a biologically active agent.

13. The device of claim 1, wherein the ports in the head are nozzles.

14. The device of claim 1, wherein the size of the ports in the head are adjustable.

15. The device of claim 1, further comprising a plurality of legs that are in communication with the handle and the head.

16. The device of claim 15, wherein each leg is fitted with a head that can deliver pressurized air.

17. The device of claim 1, wherein the applicator can communicate with a positioning system.

18. The device of claim 1, where the applicator has vibratory capabilities.

19. The device of claim 1, where the applicator has heating capabilities.

20. A method comprising:

delivering to a patient a pressurized fluid at a pressure of less then or equal to 2 bars; the pressurized fluid being generated by a device comprising:

an applicator; the applicator having a head and a handle; the head having ports that are operative to dispense a pressurized fluid; and a pressurizing section; the pressurizing section comprising at least one pump; the at least one pump being devoid of a filter, wherein the pump delivers pressurized fluid at a pressure of less than or equal to 2 bars to the applicator; where the pump has a weight of less than or equal to 10 pounds and produces less than 50 dB of noise when measured at a distance of 1 meter from a center of the pump.

21. The method of claim 20, wherein the delivering of the pressurized fluid is conducted at a pressure of less then or equal to 1 bar.

22. The method of claim 20, wherein the pressure is delivered at a substantially constant temperature for a time period of at least 30 minutes.

23. The method of claim 20, wherein the pressure is delivered at a substantially constant temperature for a time period of at least 60 minutes.

24. A method comprising:

disposing an applicator and a pressurizing section to be in fluid communication with one another; where the applicator has a head and a handle; the head having ports that are operative to dispense a pressurized fluid; and wherein the pressurizing section comprises at least one pump; the at least one pump being devoid of a filter, wherein the pump delivers pressurized fluid at a pressure of less than or equal to 2 bars to the applicator; where the pump has a weight of less than or equal to 10 pounds and produces less than 50 dB of noise when measured at a distance of 1 meter from a center of the pump.

25. The method of claim 24, wherein the applicator and the pressurizing section are in fluid communication with one another via a flexible hose.

\* \* \* \* \*